US00PP36358P2

(12) United States Plant Patent
Hansoti

(10) Patent No.: US PP36,358 P2
(45) Date of Patent: Dec. 31, 2024

(54) ***SANSEVIERIA* PLANT NAMED 'HANSOTI43'**

(50) Latin Name: *Sansevieria trifasciata*
Varietal Denomination: HANSOTI43

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 18/426,487

(22) Filed: Jan. 30, 2024

(51) Int. Cl.
*A01H 5/12* (2018.01)
*A01H 6/12* (2018.01)

(52) U.S. Cl.
USPC ..... Plt./382

(58) Field of Classification Search
USPC ..... Plt./373, 382
See application file for complete search history.

(56) References Cited

U.S. PATENT DOCUMENTS

PP33,126 P3 * 6/2021 Hansoti ..... A01H 6/12
Plt./382

* cited by examiner

*Primary Examiner* — Karen M Redden

(57) ABSTRACT

A new and distinct cultivar of *Sansevieria* plant named 'HANSOTI43' is disclosed, characterized by dark-green foliage with a wide central band of light-green/creamy-yellow streaks. The new cultivar is a compact Birds Nest type *Sansevieria* forming small plants, reaching only about 12 cm in height at maturity. Plants require little water, having a moderate tolerance for drought, and are also tolerant of very wet conditions. The new variety is a *Sansevieria,* typically produced as an indoor ornamental plant.

6 Drawing Sheets

Latin name of the genus and species: *Sansevieria trifasciata.*

Variety denomination: 'HANSOTI43'.

BACKGROUND OF THE INVENTION

The present invention relates to a new and distinct cultivar of *Sansevieria* plant, botanically known as *Sansevieria trifasciata,* of the family Asparagaceae, hereinafter referred to by the cultivar name 'HANSOTI43'.

*Sansevieria* is a monocotyledonous plant with fleshy, succulent leaves which are available in a huge range of species, varieties and cultivars as an outdoor ornamental plant (under tropical conditions) or as indoor plants.

The new *Sansevieria* 'HANSOTI43' was discovered and selected by the inventor, Ashish Hansoti, as a single aberrant side shoot within a planting of *Sansevieria trifasciata* 'Hansoti22', U.S. Plant Pat. No. 33,126, a "Hahnii" or "Birds Nest" type of *Sansevieria* grown at a nursery in Village Vangani, District Thane, Maharashtra State in Western India. 'HANSOTI43' originated as a naturally-occurring mutation of the *Sansevieria trifasciata* variety 'Hansoti22' in May of 2019.

Asexual reproduction of the new *Sansevieria* cultivar by vegetative cuttings was first performed in August 2020 at a commercial nursery in Village Vangani, District Thane, Maharashtra State in Western India. This first and subsequent propagation have shown that the distinctive combination of characteristics of the new cultivar are reproduced true to type as long as the propagation was done through side shoots (basal suckers) originating from the base of the originally discovered plant. Thus, it can be said that the new cultivar reproduces true to type through side shoots (basal suckers).

BRIEF SUMMARY OF THE INVENTION

The following traits have been repeatedly observed and are determined to be unique characteristics of 'HANSOTI43', which in combination distinguish this *Sansevieria* as a new and distinct cultivar:

1. Vivid and distinct central wide band (25 to 35 mm wide) of longitudinal lighter creamy yellow/greenish yellow streaks along length of the leaf in the center of the leaf.
2. The entire leaf, other than this broad central band is dark green (similar to the comparable cultivar, the unpatented *Sansevieria trifasciata* 'Hahnii Jade') and entirely lacking in border stripe or variegation, in contrast to its parent, 'Hansoti22'.
3. Another way to describe the new cultivar, 'HANSOTI43', would be to say its identical to its parent, 'Hansoti22' except that it has lost its border band of creamy yellow.
4. Another subtle difference between the new 'HANSOTI43' and its parent cultivar (*Sansevieria trifasciata* 'Hansoti22') is the leaf length in 'HANSOTI43' it is somewhat shorter in a plant of similar age, giving the rosette a more compact and tighter look.

Leaf width is quite variable and the strongest, healthiest plants have the widest leaves this is true across all *Sansevieria trifasciata* cultivars known to the inventor. This variation means leaf width can be anything from 5 cm to 8 cm wide depending on season, growing conditions and plant vigour and plant age. Typically, the leaves are of medium width (about 6 cm average measured at the widest part of the mature leaf under good growing conditions) and lanceolate with a firm, waxy texture. The blades are thick and fleshy.

The new variety 'HANSOTI43' is a variety of *Sansevieria* in the group denominated as "Birds Nest" or 'Hahnii' types based on its origin and overall plant form. The new variety presents an average of 12 leaves per plant when it reaches maturity (about 3 months from rooted liner) but over time it can grow and accumulate many more leaves and increase in overall height.

The new variety is moderately drought tolerant and adapts well to conditions of bright light or heavy shade (exterior and interior). The intensity of leaf colour varies with exposure to light and the contrast is most intense under high light conditions.

The leaves show a variegated colouration, with the whole leaf of dark green and a central area longitudinally marked by a distinct band consisting of lighter creamy green streaks.

The dark green background coloration of the leaf shows colouration similar to RHS Green 136A. The transverse horizontal bands so typically seen in most *Sansevieria trifasciata* cultivars are essentially absent on the dark green background but are indistinctly seen on the central lighter band. The characteristic (and unique to 'HANSOTI43') light greenish to creamy yellow band of streaks range from Yellow-Green N144C to 144A.

To put it in another way, the creamy-yellow border forms 5 to 10% of the leaf width in the parent *Sansevieria trifasciata* 'Hahnii Marginata' but consistently forms 30 to 50% and sometimes even more of the width of the leaf in the invention, 'HANSOTI43'.

The backside of the leaves has similar coloration (the green background is slightly lighter, nearer RHS Green 136B) except that the typical *Sansevieria trifasciata* transverse horizontal banding is more visible. Though not prominent is still more obvious compared to the top surface of the leaf. The broad band of streaks seen on top of the leaf is also seen at the bottom surface and is similarly coloured but is slightly less prominent.

Attached colour pictures are a better guide to the overall colouration and variegation pattern rather than written descriptions. The primary distinctive characteristic is the lighter longitudinal broad band consisting of light greenish to creamy yellow streaks within the broad darker green leaf.

PARENTAL COMPARISON

Plants of the new *Sansevieria* 'HANSOTI43' are similar to plants of the parental cultivar, however, 'HANSOTI43' differs in the characteristics described in Table 1.

TABLE 1

| | Characteristic | Parent Cultivar 'Hansoti22' 'Star & Stripes' | New cv 'Hansoti43' |
|---|---|---|---|
| 1. | Leaf size | 10 to 13 cm long | 9 to 11 cm long |
| 2. | Number of leaves | 9 to 12 leaves | 10 to 13 leaves (More leaves) |
| 3. | Variegation Pattern | Cream border on dark green leaves plus wide central band of light green/creamy yellow streaks. | Dark green leaf with wide central band of light green/creamy yellow streaks. No border to the leaf whatsoever. |
| 4. | Border variegation | 1 to 9 mm wide cream border | No border variegation. |
| 5. | Central Variegation | 20 to 30 mm wide band of lighter green/creamy yellow streaks | 20 to 30 mm wide band of lighter green/creamy yellow streaks |

COMMERCIAL COMPARATOR

Plants of the new *Sansevieria* 'HANSOTI43' are similar to the commercial variety *Sansevieria trifasciata* 'Hahnii Jade', unpatented. Plants of the new *Sansevieria* 'HANSOTI43' differ from plants of the commercial cultivar in the characteristics described in Table 2.

TABLE 2

| | Characteristic | Similar Cultivar 'Hahnii Jade' (unpatented) | New 'Hansoti43' |
|---|---|---|---|
| 1. | Leaf | 10-13 cm long | 9 to 11 cm long |
| 2. | Number of leaves | 10-13 leaves | 10 to 13 leaves |
| 3. | Variegation Pattern | Dark green leaves with no variegation or longitudinal streaks and no hint of transverse banding typical of *S. trifasciata* cultivars. | Dark green leaf with wide central band of light green/creamy yellow streaks. Transverse banding present but very subdued and seen only within the areas marked by the central streaks. |
| 4. | Border variegation | None | No border variegation. |
| 5. | Central Variegation | None - full leaf is uniform dark green. | 20 to 30 mm wide band of lighter green/creamy yellow streaks |

BRIEF DESCRIPTION OF THE PHOTOGRAPHS

The accompanying photographs illustrate the overall appearance of the new *Sansevieria* cultivar 'HANSOTI43' showing the colors as true as is reasonably possible with colored reproductions of this type. Colors in the photographs may differ slightly from the color value cited in the detailed botanical description which accurately describe the color of 'HANSOTI43'.

These pictures illustrate the plant form which is the unique characteristic of 'HANSOTI43' and at the same time demonstrates that plant coloration and variegation pattern is similar to several other *Sansevieria trifasciata* cultivars. All plants were grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions). These conditions closely approximate those used in commercial practice in India.

Figure 1:
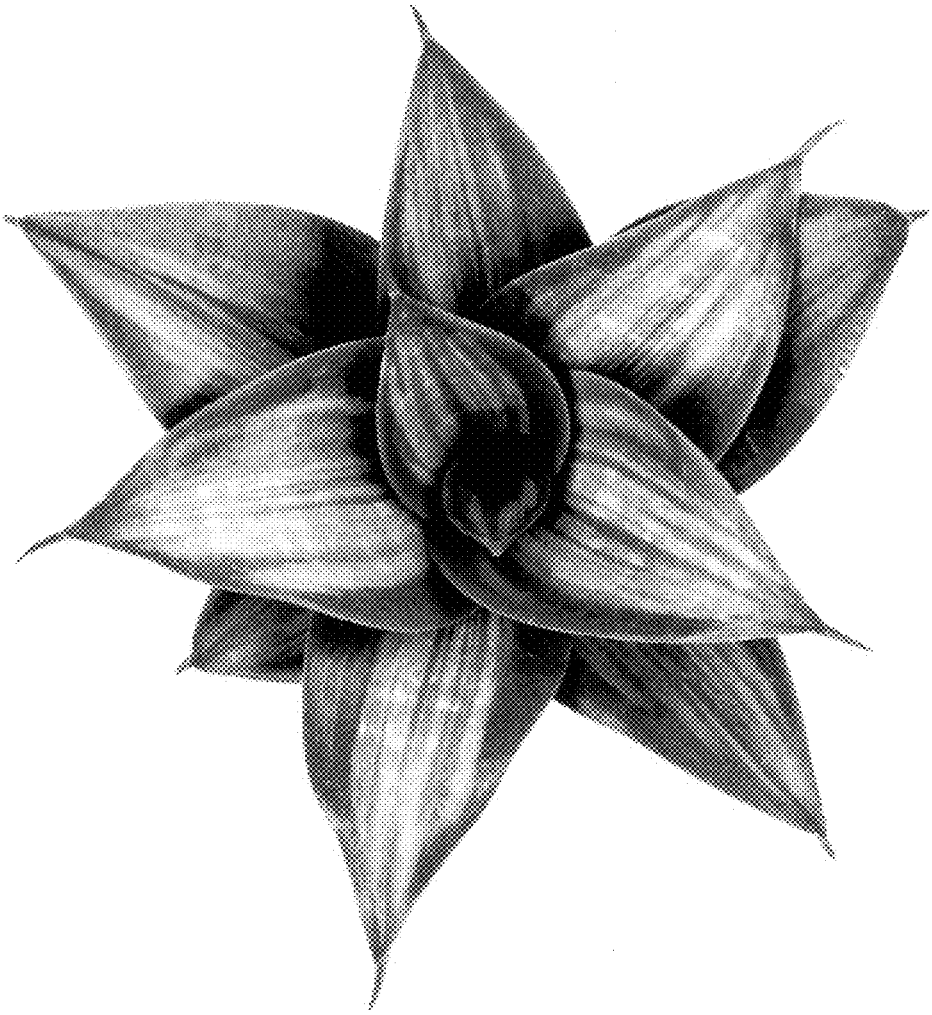
FIG. 1 shows a top view of a three-month old (from rooted liner) plant of *Sansevieria* 'HANSOTI43' in a 12 cm diameter pot.
Figure 2:
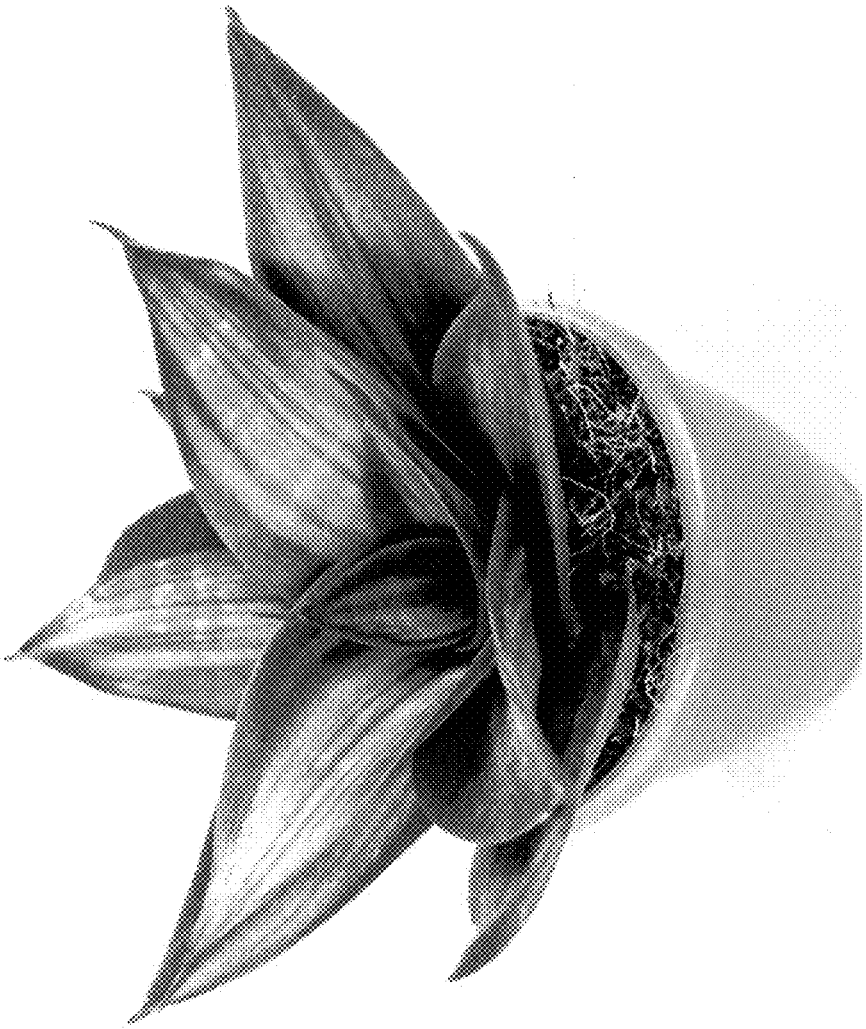
FIG. 2 shows a side view of a plant of 'HANSOTI43'.
Figure 3:
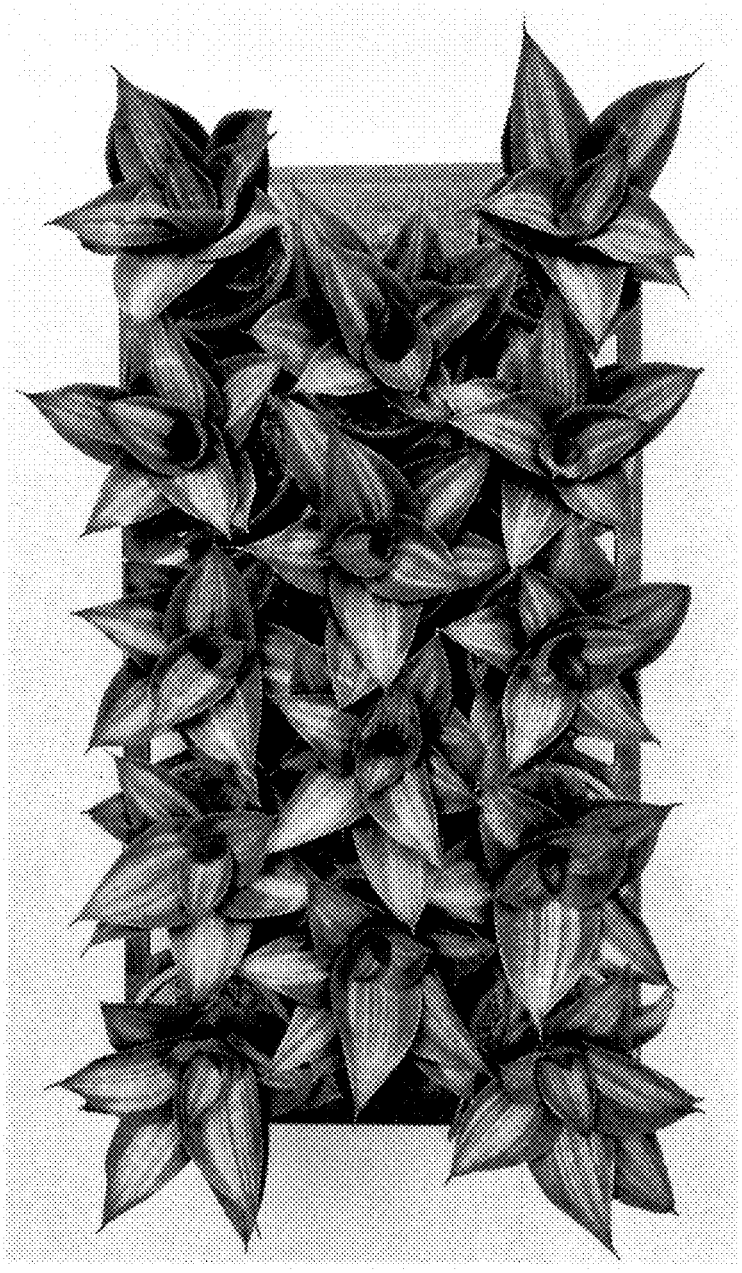
FIG. 3 shows a group of 14 'HANSOTI43' plants in a tray, showing uniformity across multiple plants of this new cultivar.
Figure 4:
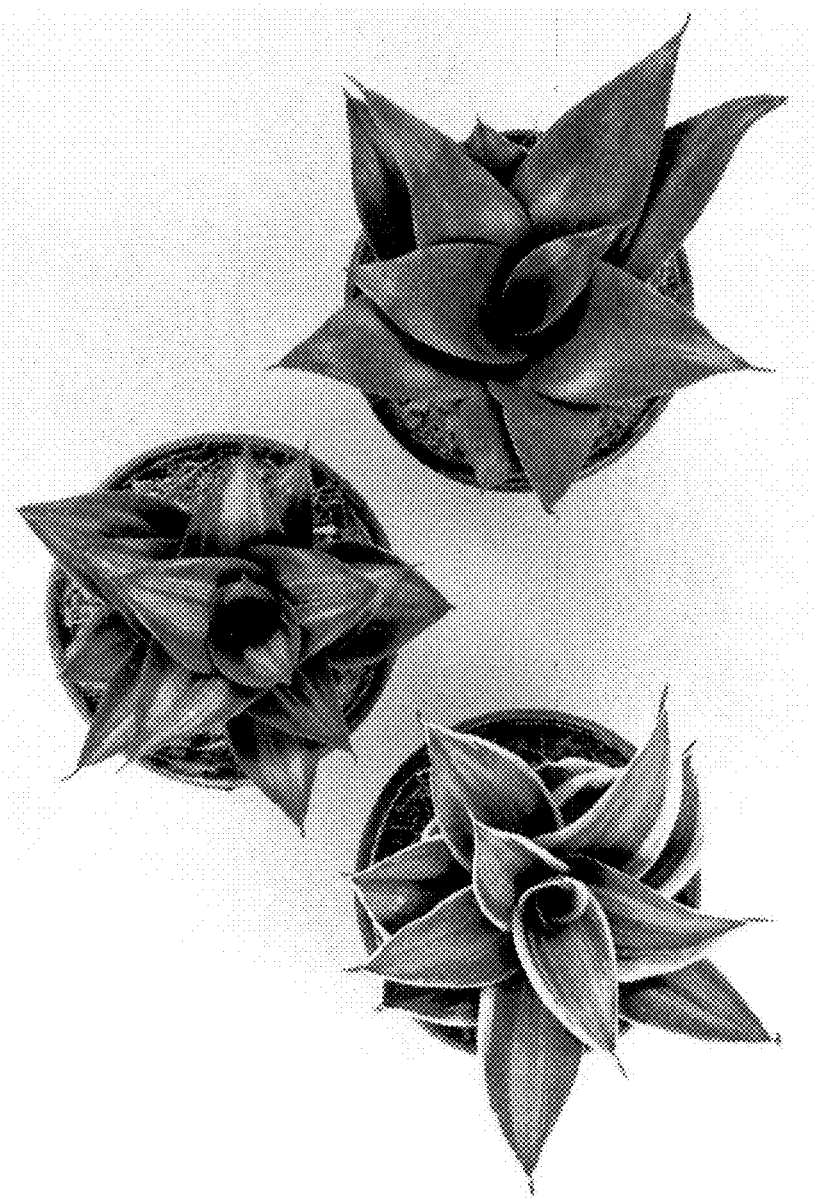
FIG. 4 shows the parent plant *Sansevieria trifasciata* 'Hansoti22' (bottom left) alongside a plant of the similar cultivar *Sansevieria trifasciata* 'Hahnii Jade' (bottom right) and 'HANSOTI43' (top center) to compare the three.
Figure 5:
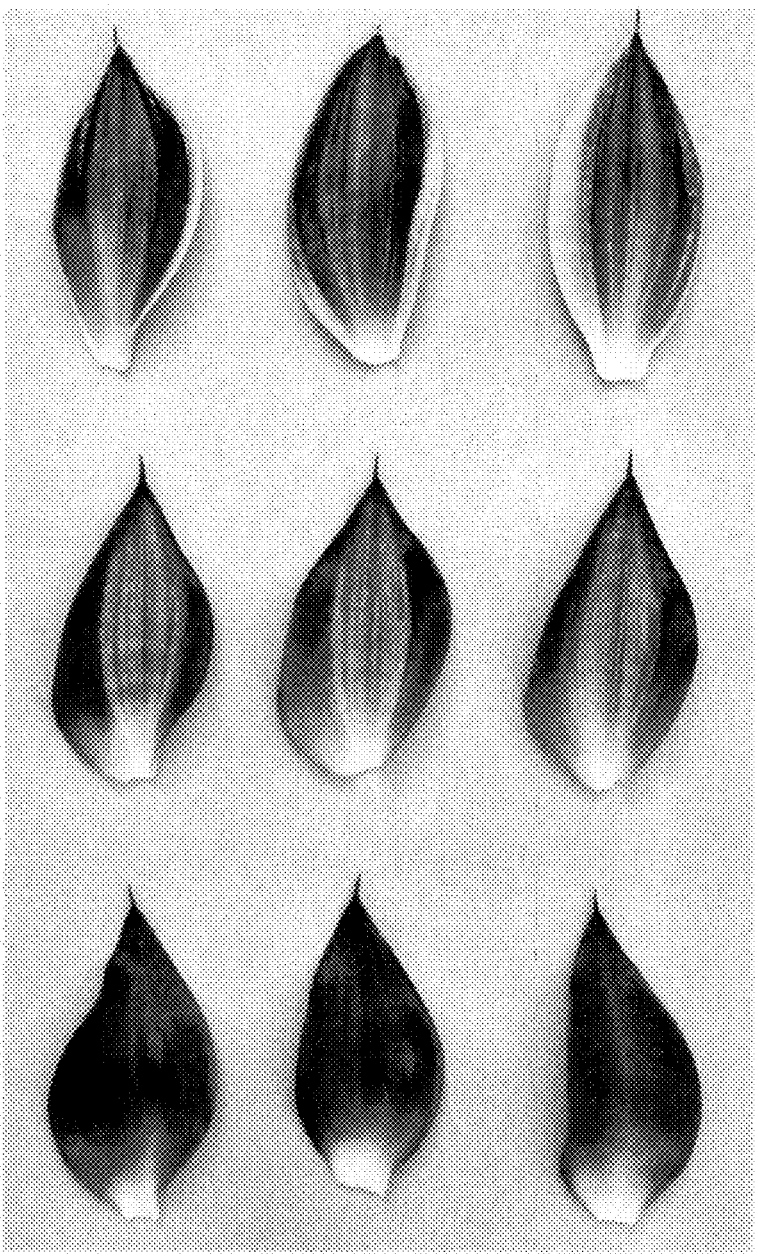
FIG. 5 is a comparison of individual leaves of *Sansevieria* 'Hansoti22', the parental variety, (top row) and leaves of the comparable cultivar *Sansevieria trifasciata* 'Hahnii Jade' (bottom row)—with leaves *Sansevieria* 'HANSOTI43' (center row) the absence of leaf border along leaf edge, and novel streaking in the center of leaves of 'HANSOTI43' is very obvious.
Figure 6:
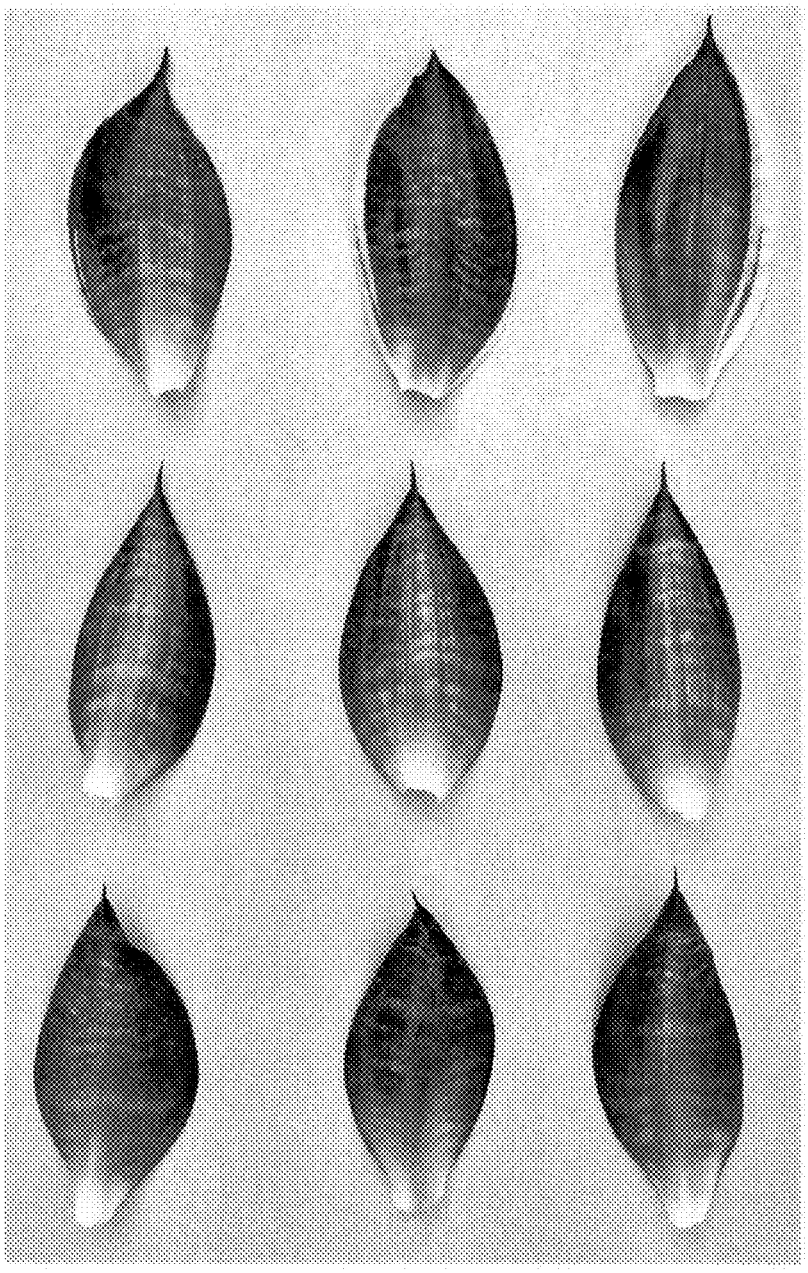

FIG. 6: Shows a comparison of the bottom (abaxial) surface of individual leaves of *Sansevieria trifasciata* 'Hansoti22' (top row) the parental variety-as well as leaves of *Sansevieria trifasciata* 'Hahnii Jade' (bottom row) with leaves *Sansevieria* 'HANSOTI43' (center row) to allow comparison between all three cultivars.

DETAILED BOTANICAL DESCRIPTION

The new *Sansevieria* 'HANSOTI43' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI43' plants grown in an open poly house (high tunnel) at Village Asle, District Satara, Maharashtra State in Western India. Average temperature in Asle is 25° C., with summer highs of 39° C. and winter lows of 6° C. Plants grow under natural light conditions and between 30% to 75% shade levels depending on the season (higher shade in hot summer conditions).

This crop gets nearly constant fertilization to increase production. Controlled release fertilizer of slow release 13:11:11 Type 360-days release at 1 kilo/cubic meter of media, Constant Liquid Feed at approximately 100 ppm N, 20 ppm P and 100 ppm K, along with complete micronutrients. Production is closely related with proper and complete plant nutrition and an open soilless growing media based on coconut coir. The plants are grown in plastic pots on metal benching in spacing trays.

Color references are made to The Royal Horticultural Society Colour Chart (R.H.S.), (April 2009) except where general colors of ordinary significance are used.

The photographs and descriptions were taken during the monsoon season in Asle, District Satara, Maharashtra State, India when outdoor day temperature was 25° C. to 30° C., and nighttime temperatures of 10° C. to 15° C. The age of the plants described is 3-4 months.

Botanical classification: *Sansevieria trifasciata* 'HANSOTI43'.

General information:

*Parentage.*—*Sansevieria trifasciata* 'Hansoti22', U.S. Plant Pat. No. 33,126.

*Optimal growth conditions.*—Light intensities: High adaptability to outdoor or indoor conditions. Temperature: Day: 25° C. to 35° C. Night: 15° C. to 25° C. Temperature tolerance: Tolerant to a low temperature of about 6° C. and a high temperature of 38° C. and above — very heat tolerant. Fertilization: Constant feed of 100 ppm N, 20 ppm P and 100 ppm K is used along with micronutrients with occasional leaching. Growth regulators: Not necessary for growth, however rooting hormone aids in rapid and prolific rooting of offsets.

Propagation:

*Typical.*—Vegetative, by side suckers which come true to type. Does not come true from leaf cuttings.

*Rooting habit and description.*—Rhizomes are elongated, fleshy, giving rise to offsets (side shoots). Offsets root easily with fibrous adventitious roots from cut end. Rooting hormone helps in faster and more prolific rooting. Colored cream to brown, not accurately measured with R.H.S. chart.

*Time to initiate roots.*—15 to 20 days at 25° C. to 30° C.

*Time to produce a rooted liner.*—About 45 days at 25° C. to 30° C.

*Time to produce ready* 12 *cm potted plant from liner.*—About 3 months at 25° C. to 30° C.

Plant:

*General appearance and form.*—Monocot; leaf bases arranged in a rosette around growth point.

*Height.*—About 10 to 12 cm when grown in 12 cm pots.

*Spread.*—About 15 to 17 cm when grown when grown in a 12 cm size container.

*Growth rate and habit.*—Moderate growth rate, stays flat and compact.

*Shape.*—Rosette.

*Fragrance.*—None.

*Stem.*—Modified (rhizomes which are fleshy with erect foliage, branching and giving offsets so forming clumps in time).

*Rosette height.*—About 10 to 12 cm height from top of pot when grown in 12 cm size container.

*Rosette diameter.*—About 15 cm to 17 cm.

*Texture.*—Smooth, waxy.

*Colour.*—As described above.

*Strength.*—Strong and durable.

*Internode length.*—About 1 mm.

Foliage:

*Quantity.*—About 10 to 14 in ready to sell plant. Number slowly increases with age.

*Arrangement and attachment.*—Single, alternate; leaf bases arranged stiffly in a rosette around central growth point.

*Leaf length.*—About 10 to 12 cm, full-size leaf.

*Leaf width.*—About 5 to 6 cm, full-size leaf.

*Overall shape of leaf.*—Lanceolate.

*Apex shape.*—Acute, triangular and aristate, with soft tip.

*Base shape.*—Plane.

*Margin.*—Sharp, smooth.

*Texture.*—Upper Surface: Smooth and waxy texture.

*Texture.*—Under Surface: Smooth and waxy texture.

*Pubescence.*—None.

*Color of mature leaf.*—Upper Surface: Basal dark green colour near RHS Green 136A with a central wide band with streaks of Yellow-Green N144C to N144D. Cross hatching, or transverse bands so typical of *Sansevieria trifasciata* cultivars not seen.

*Margins.*—Same dark green as rest of leaf. No border at all.

*Color of mature leaf.*—Lower Surface: Similar to the adaxial surface but a shade lighter (nearer RHS Green 136B) and with reasonably obvious transverse banding seen. The longitudinal band of streaks still obviously seen.

*Crossbanding.*—Barely discernible on top surface; visible but indistinct on bottom surface of leaf.

*Venation.*—Pattern: Longitudinal/parallel leaf shape.

*Venation color.*—Indistinguishable from leaf blade.

*Leaf fragrance.*—None.

Other:

*Inflorescence description*.—Flowers not observed to date.

*Weather resistance*.—Moderately drought tolerant.

*Pest resistance*.—Reasonably resistant to pests, susceptible to root mealybugs (*Rhizoecus pritchardi*). Typical pests include *Pseudococcidae longispinus* and *Tetranychus urticae*.

*Disease resistance*.—Shown to be more resistant to *Anthracnose* than *Sansevieria trifasciata* 'Hahnii Jade'.

*Fruit/seed production*.—No fruits/seeds detected to date.

What is claimed is:

1. A new and distinct cultivar of *Sansevieria* plant named 'HANSOTI43' as herein illustrated and described.

* * * * *